United States Patent [19]

Truett

[11] Patent Number: 5,723,341
[45] Date of Patent: Mar. 3, 1998

[54] SCREEN CELL AND METHOD OF USING

[75] Inventor: William L. Truett, West Brattleboro, Vt.

[73] Assignee: Janos Technology Inc., Townshend, Vt.

[21] Appl. No.: 675,553

[22] Filed: Jul. 3, 1996

Related U.S. Application Data

[63] Continuation-in-part of Ser. No. 496,058, Jun. 28, 1995, abandoned, which is a continuation-in-part of Ser. No. 201,797, Feb. 25, 1994, Pat. No. 5,453,252.

[51] Int. Cl.$^6$ .......................... G01N 21/62; G01N 21/01
[52] U.S. Cl. ...................... 436/171; 436/174; 422/82.09; 422/104; 356/244; 356/246; 356/440
[58] Field of Search .................... 422/82.05, 102, 422/82.09, 104; 356/244, 246, 440; 446/15, 21, 16; D21/61; 250/459.1, 458.1; 436/165, 171, 174

[56] References Cited

U.S. PATENT DOCUMENTS

| | | |
|---|---|---|
| 3,873,268 | 3/1975 | McKie, Jr. . |
| 4,682,890 | 7/1987 | De Macario et al. ............... 356/244 |
| 5,095,213 | 3/1992 | Strongin ............................. 250/459.1 |
| 5,290,705 | 3/1994 | Davis .................................. 436/164 |

*Primary Examiner*—David A. Redding
*Attorney, Agent, or Firm*—Herbert M. Wolfson

[57] ABSTRACT

A method of analyzing a specimen by infrared spectroscopy is disclosed wherein a specimen support having a plurality of unobstructed holes of substantially uniform size and a film of the specimen enclosing each hole is positioned vertically in the spectrometer and a beam of infrared light is directed through the holes to generate a wavelength spectrum characteristic of the specimen.

8 Claims, 4 Drawing Sheets

Fig. 4
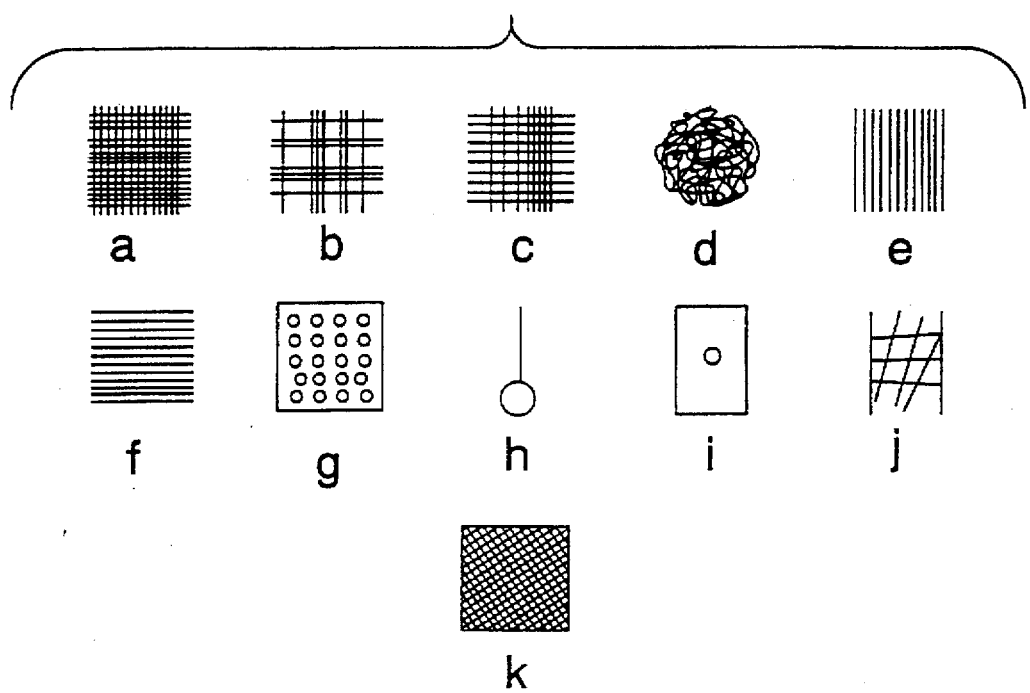
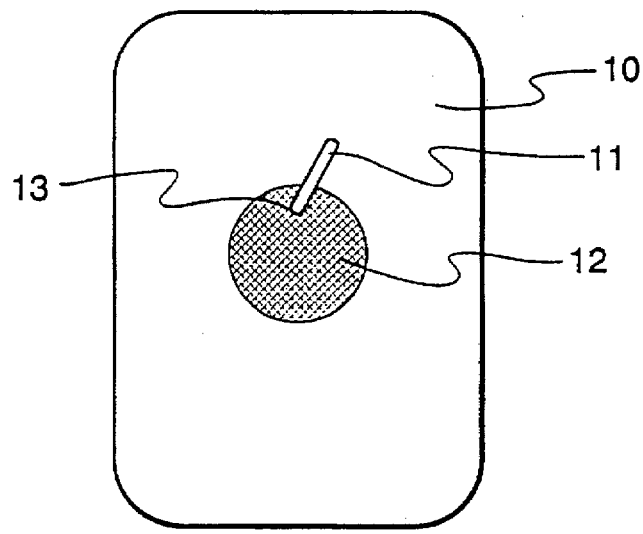
Fig. 5

SCREEN CELL AND METHOD OF USING

CROSS REFERENCE TO RELATED APPLICATION

This application is a continuation-in-part of U.S. application Ser. No. 08/496,058 filed Jun. 28, 1995, now abandoned, which was a continuation-in-part of U.S. application Ser. No. 08/201,797 filed Feb. 25, 1994, now U.S. Pat. No. 5,453,252.

FIELD OF THE INVENTION

This invention is concerned with placing a liquid, a paste, powder or solid sample on a screen in order that a spectrum can be determined in a spectrometer, with the screen being fixed to a holder which permits the screen to be placed vertically in the energy beam of the spectrometer that projects the beam horizontally.

BACKGROUND OF THE INVENTION

The art of placing samples in spectrometers is a very old one and was well developed prior to 1940. Although developments in placing samples in spectrometers in order that their spectra may be determined is very well established in infrared spectrometers and, in particular, in Fourier Transform Infrared (FTIR) Spectrometers, parallel developments have taken place in UV spectrometers, visible light spectrometers, near infrared spectrometers, far infrared spectrometers, Raman spectrometers and fluorescence spectrometers to achieve similar results. The attention in this disclosure will largely be concentrated on the FTIR spectrometer.

In order to determine qualitative spectra of liquids, or solutions of solids and pastes, several methods have been developed. FIG. 1 shows a device known as a demountable cell. Two suitable windows of IR transmitting material, such as sodium chloride 1 are held in place by a retaining ring 2 which is held in position by three bolts and nuts on a mounting plate 4 which fits into the cell slide of a commercial FTIR spectrometer. The cell slide insures that the sample held between the windows 1 will be in the energy beam of the spectrometer. The demountable cell of FIG. 1 is loaded by placing one or two drops of liquid between the windows 1 and placing the windows 1 on the plate 4, attaching the retainer ring 2 to upright bolts 3 and placing a nut on each bolt 3 and tightening down to desired level. The cell is simple to assemble and disassemble, but the sodium chloride windows are expensive, subject to attack by moisture and many solvents, and is fragile.

FIG. 2 depicts a card 5 containing a porous polyethylene or porous polytetrafluoroethylene window 6 upon which a sample of liquid or solution of a solid, or a paste can be placed. The card, FIG. 2, is then placed in the cell slide of an FTIR spectrometer and a spectrum is determined. The problem with this device is that the spectrum of the porous paper is also determined in addition to that of the sample applied to the card window. This complicates the interpretation of the IR spectrum and renders information in four critical areas of the spectrum uncertain in the case of the polyethylene window. Several valuable areas are also useless when polytetrafluoroethylene paper is used.

Infrared microspectroscopy is the subject of U.S. Pat. No. 5,290,705 to Davis. This patent discloses a specimen support having a plurality of unobstructed holes, which holes may have a diameter in the range of 10 microns to 13 millimeters. Davis discloses a method for analyzing a liquid specimen where an unsupported film of a liquid specimen encloses each hole; the support is positioned horizontally in the microspectrometer so that the axis of the holes are vertical; and the beam of infrared light is directed vertically through the film of the liquid specimen enclosing the holes to provide a wavelength spectrum characteristic of the liquid specimen.

The object of the present invention is to provide a method for analyzing a liquid specimen using a conventional infrared spectrometer that projects a light beam horizontally, i.e. along a horizontal axis.

Another object is to provide a specimen support that can be positioned vertically but designed to retain the liquid specimen for a sufficient time of exposure to the light beam to produce an accurate and reproducible analysis of the specimen.

Other objects will appear hereinafter.

SUMMARY OF THE INVENTION

The objects are accomplished by first applying a liquid specimen to a screen in such a fashion that even though the screen is in a vertical position, it retains a thin layer or film of the sample. When the screen is placed in the sample compartment of the IR Spectrometer, in the vertical position, a spectrum is easily obtained. The advantages of such a cell are many. First, the device is simple to use and, if desired, cleaning is quite easy; second, it can be used in any wavelength range of the electromagnetic spectrum from the vacuum UV to the far IR; third, there is no corrosion or wear as well as no fragility; fourth, the screen cell is modest in cost, can easily be reused in many cases and can be discarded with no hazard to the environment.

To enable the screen cell to be used successfully in the vertical position with the scanning beam directed horizontally through the sample to be analyzed, the dimensions of the aperture or openings of the screen are critical. In order for a liquid sample of at least about 0.1 microliter (the minimum amount for a successful reading) to be retained as a film over each opening for a sufficient time to be analyzed and be thin enough to be analyzed successfully with a minimum opportunity for error, the longest dimension of the opening must be no greater than about 2 millimeters, preferably no greater than 1 millimeter; and, in order to be read at all in the spectrometer i.e., contain at least 0.1 microliter, the opening must be at least 0.1 millimeter, preferably at least about 0.5 millimeter. Thus, for a substantially square or rectangular screen opening, each unobstructed (usually contiguous) hole or aperture will have a cross-sectional area of from 0.01 to about 4 square millimeters, preferably in the range of about 0.9 to 1.1 square millimeters, most preferably 0.25 to 1 square millimeter.

A longest dimension of greater than 2 millimeters makes most films of liquid materials fail to cling well or long enough in the screen cell for a successful reading to be taken in the spectrometer. The force or pull of gravity tends to overcome the surface tension of the liquid for the cell to be used in the vertical position.

It is recommended to apply the liquid sample to a screen cell held in the horizontal position to obtain a uniformly thin film layer before inserting the cell in the vertical position in the spectrometer. This procedure will provide sufficient time for a successful reading to be obtained. The surface tension of the liquid will be sufficient to prevent loss of the film sample to gravity and the time (4 seconds) will be enough to prevent evaporation of the liquid sample.

Although the screen cell of this invention is usually composed of a plurality of square or rectangular openings of uniform area or size, other shaped openings can be used. Thus, triangular, hexagonal, octagonal or other polygonal apertures are possible as well as circular, elliptical, etc. As long as the longest dimension of the particularly shaped opening is at most about 2 millimeters, preferably 1 millimeter, and the shortest dimension no shorter than about 0.1 millimeter, preferably 0.5 millimeters, it will be possible to obtain a thin liquid film sustainable in the vertical position through which a horizontally directed beam can provide an accurate analysis in the spectrometer.

In the most preferred practice of the method of the present invention from the standpoint of accuracy and speed, it is important that the unobstructed openings of the screen cell should be all uniformly sized and such that the sample's surface tension is sufficient for the sample to be retained on the cell at least 4 seconds for the spectrometer to obtain a reproducible and accurate FTIR spectrum while the number of cell openings are not so numerous as to permit at least 25% of the light energy generated by the spectrometer to pass through the liquid sample.

It has been found that the size of the openings in the most preferred screen cell used in accordance with the present invention be no greater in diameter or longest dimension (for a non-circular opening) than about 1 millimeter and no smaller than 0.5 millimeter for liquids such as water, isopropyl alcohol and acetone (the most common solvents used for analytical work). Use of openings of about 1 millimeter will retain the sample in the vertical position for about 5 seconds; while openings of 2 millimeters may not retain all such liquids for the 4 seconds required to determine the FTIR spectrum.

It was also found that the use of a cell with 1 millimeter openings or apertures provided an energy level from the blank screen cell in the spectrometer of about 50%. Reducing the openings to 0.5 millimeter provided a retention time in the vertical position with the previously mentioned solvents of about 10 seconds and, in most configurations, provided an energy level of about 25%, the minimum required for an adequate spectral determination using FTIR.

Thus, the most preferred opening size in the screen cell when used in a vertical position for obtaining a minimum retention of at least 4 seconds and an energy level of at least about 25% of the energy transmitted through the cell is from 0.5 millimeter to about 1 millimeter.

OTHER EMBODIMENTS OF THE INVENTION

In addition to the application of the screen cell to liquids or solutions, it may also be used for pastes or powders which can be smeared onto the screen. The use of the screen cell to determine the spectra of solids can be achieved in several ways. In one, the solid is dissolved in a suitable volatile liquid which is then applied to the screen and upon evaporation, leaves a thin layer. The screen is then inserted vertically in a suitable spectrometer, as a Fourier Transformer IR spectrometer, and a spectrum is determined. One can also place the screen cell on a flat metal surface, apply the powdered solid to the screen, add a second piece of flat metal, place the metal screen—metal sandwich in a high pressure press and generate a clear film of the solid. Such films tend to be thicker than those generated by solvent deposition; but using the critical size of openings in the screen cell, the cell can be used successfully when placed in the vertical position in the spectrometer.

The advantages of this technique for solids are similar to those given for liquids. However, the screen can not be reused. The cost is still modest and discarding is a minor problem. Unlike the screen cell used with liquids, the screen cell used with solids can be stored very nicely and permanent collections maintained.

Although the technique of the screen cell works well with FTIR spectrometers, it is not so limited. The technique will find application in the following types of spectrometers: vacuum UV, UV, Visible light, NIR, FIR, Raman and fluorescence, particularly when the cells in these spectrometers are used in the vertical position.

The application of pastes to the screen is not difficult. A small spatula is used to spread material into a transmissive layer. The application of a thin film of powder can be done in a similar fashion, the powder being spread on the screen cell into a thin transmissive layer.

In addition to ease of measurement by transmission through the cells mounted vertically in spectrometers, it is also possible to analyze samples applied to screen cells by various means in various reflection modes. Samples can be examined by diffuse reflection and/or specular reflection when necessary accessories are available for the various spectrometers.

When the scrim type of screen is in use in the cell, a reagent or reagents can be placed on the screen to react with a sample applied to the screen. In this fashion, blood analysis or urinalysis can be carried out and the analytical results determined using the appropriate spectrometer.

One critical property of the screen cell is that the cell transmit sufficient energy in order to determine a spectrum with the desired spectrometer. A second critical property of the screen cell is that it has no absorption spectrum when placed in the spectrometer. All screen cells of this invention meet these two essential criteria.

BRIEF DESCRIPTION OF THE DRAWINGS

FIG. 4 is a series of front views of various screen types useful in this invention;

FIG. 5 is a front view of a peg holder on a plate for holding the screen;

DETAILED DESCRIPTION OF THE DRAWING AND A PREFERRED EMBODIMENT OF THE INVENTION

Figure 1:
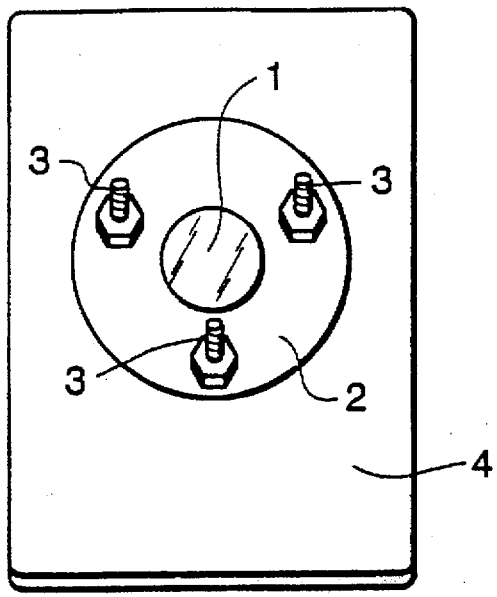
FIG. 1 is a front view of a demountable cell holding two windows.
Figure 2:
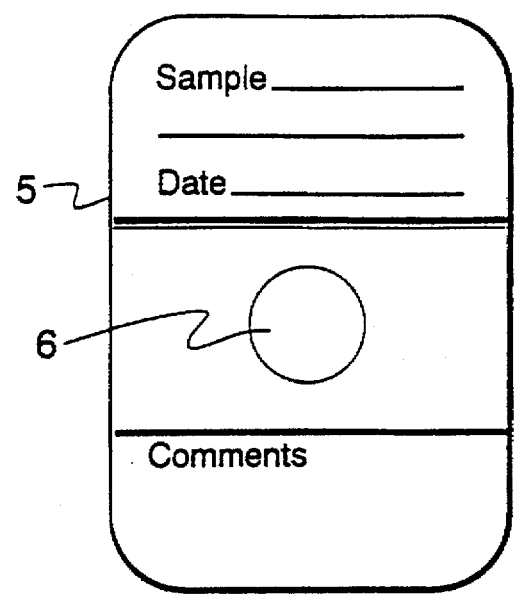
FIG. 2 is a front view of a cardboard holder or a polyethylene paper cell.
Figure 3:
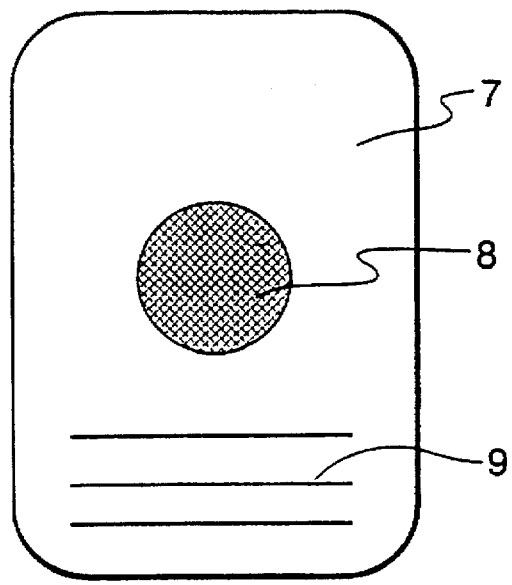
FIG. 3 is a front view of a screen cell of this invention.

The screen cell in FIG. 3 consists of a holder 7 to which a screen 8 is attached by a suitable means such as adhesives, adhesive tape, Velcro, and an identifying legend 9 which is positioned in the cell slide of any desired spectrometer.

The purpose of the screen cell shown in FIG. 3 is to facilitate the rapid qualitative spectrum of liquids, pastes, powders, and solids. The infrared spectrometer, specifically the Fourier Transform IR Spectrometer, will be used to illustrate the recommended technique. However, the screen cell is broadly applicable to all types of spectrometers, including but not limited to the following: Vacuum UV, UV, Visible light, Near Infrared (NIR), Infrared, Far INfrared (FIR), Fluorescence and Raman. In each case, the holder geometry can be easily adapted to the sample holder of the spectrometer in use. In the case of the IR spectrometer, all of the IR instruments have uniform dimension cell slides which will accept holders.

The precise nature of the screen can vary dependent upon the usage. Basically, the screen types which can be employed in the screen cell are shown in FIG. 4. FIG. 4A is the classical screen grid normally seen in window screens and is substantially uniform with regard to the apertures at about 0.1–2 millimeters. In addition to the uniform screen, non-uniform screens are also manufactured as in FIG. 4b as well as non-uniform screens with graded changes in aperture. FIG. 4c is an additional type for use in screen cells. It is a chaotic mesh of the sort that would be realized from the use of glass wool. FIG. 4d, although the grid type of screen is the preferred type, the parallel types shown in FIG. 4e and FIG. 4f are also applicable for use in the screen cell. It is also possible to use screen like materials with non-contiguous openings such as the perforated plates shown in FIG. 4g. Two other types are of interest, FIG. 4h which is a screen with random apertures, and FIG. 4i is screen commonly known as a scrim which is usually a tight network of fibrous materials. The latter case of FIG. 4k has the appearance of a thin sheet of paper, however, sufficient energy to determine a spectrum may be passed by this type of screen. However, it does not possess a spectrum in the infrared. In all cases, it should be understood that the openings should be adjusted preferably to a maximum size of 0.5–1 millimeter for successful use of the cell in the vertical position in the spectrometer.

A wide range of materials of construction can be utilized for the screens. materials can be utilized. Screens may be prepared from glass fibers with a coating of polymers, usually poly (vinyl chloride), and screens from quartz fibers may be used as well as screens fashioned from various metals and metal alloys, including the noble metals. Ceramic materials can be fabricated into screens, as can a very wide variety of plastic and elastomeric materials, such as nylons, polyphenylene sulfide, PEEK, polybutadiene and silicone polymers. The use of textile fibers both synthetic and natural can be considered for special purposes, very likely one-time uses, as in the application of screen cells to medical analysis.

FIG. 5 showing a peg holder for the screen cell is an alternate to the FIG. 3 screen cell with the screen attached by adhesive. FIG. 5 shows a peg holder 11 mounted on cardboard or plastic plate 10 with a screen 12 attached by means of the peg fitted into a hole 13 in the screen.

Figure 6:
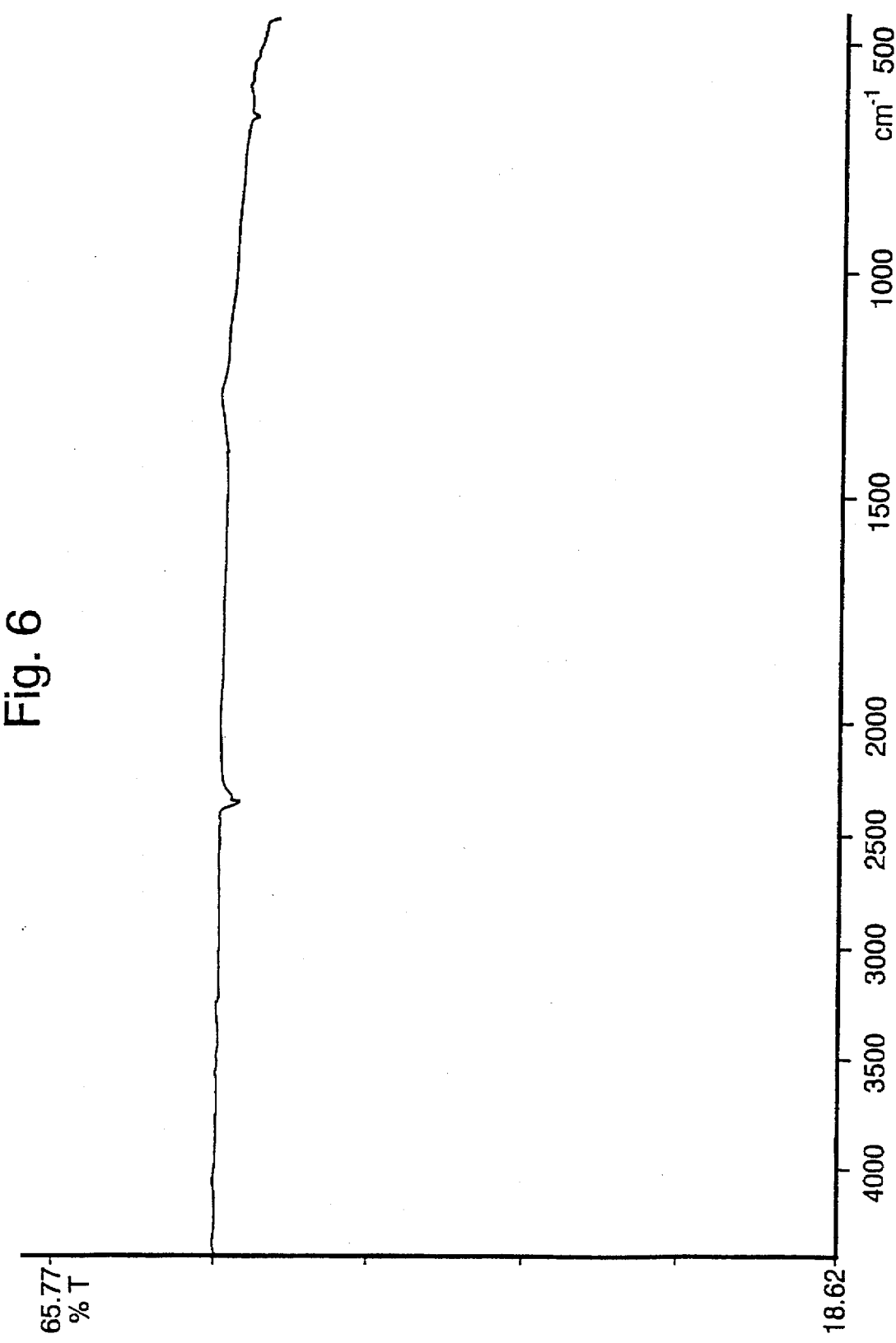
FIG. 6 is a background spectrum obtained using the screen cell of this invention.
Figure 7:
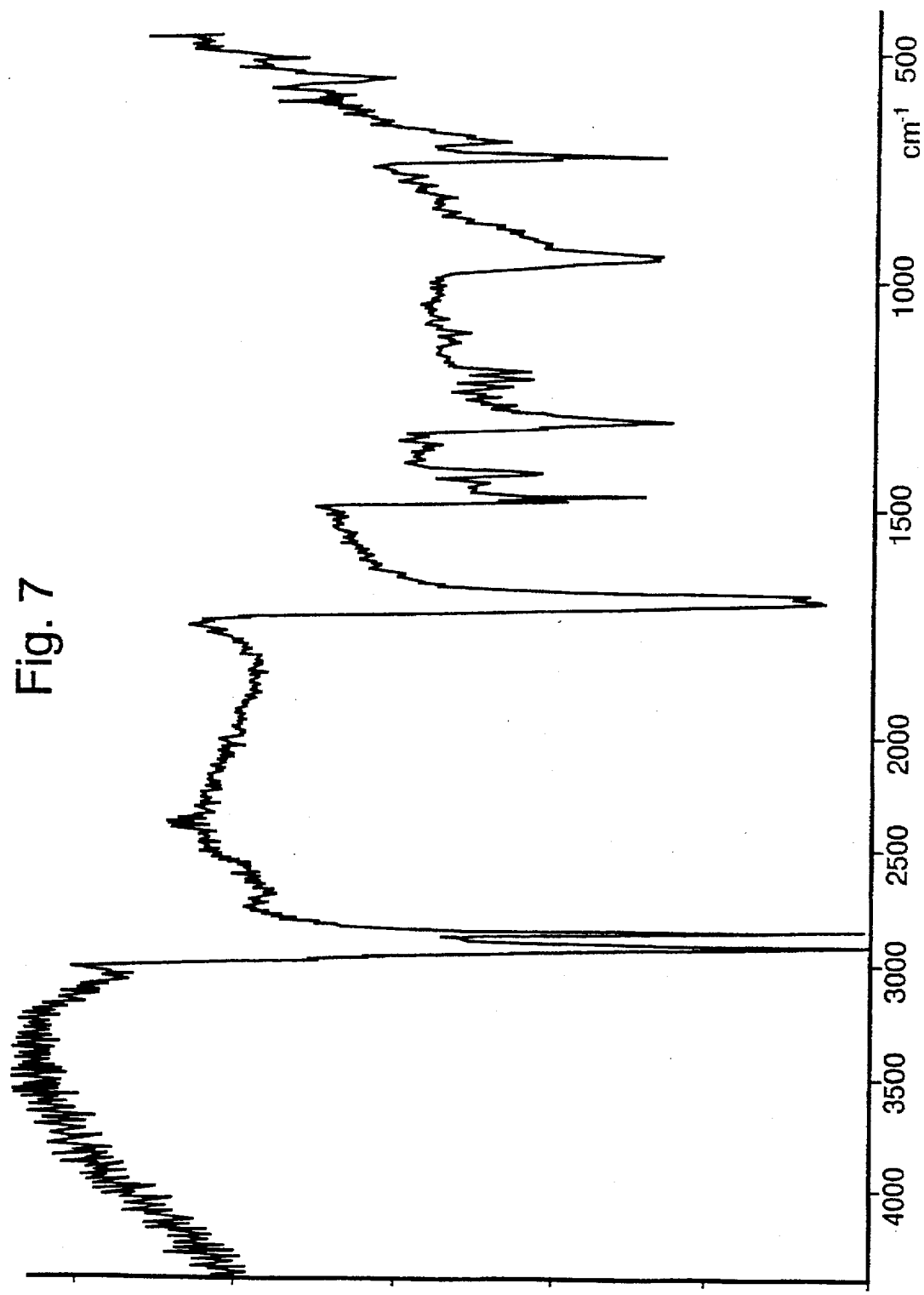
FIG. 7 is a spectrum of stearic acid obtained using the screen cell of this invention.

FIG. 6 is a background spectrum of the screen cell which clearly indicates that the screen cell has no infrared absorbance in the range of 4,000 to 500 cm. FIG. 7 is an example spectrum of stearic acid using the screen cell in a spectrometer.

The materials of construction of the holder for the screen portion of the screen cell are many. The paper or cardboard holder will be the most common, but the mode of affixing the screen to the holder need not be solely the adhesive type; the screen can also be affixed to the holders by placing a Velcro strip on the holder and screen, or via using a strip of durable stick tape on the face of the holder, or by placing one or more hooks on the holder, which engage perforations in the screen. The holder materials can be: paper, cardboard, plastic, metal, metal alloys, glass, ceramic and elastomers.

The use of multiple screens is a modification of the single screen cell which has the advantage that a greater thickness of sample can be realized. This would be convenient with techniques such as NIR spectroscopy that requires a thick sample. An additional advantage of multiple screens is that the sample of liquids is less likely to evaporate.

Application of the screen cell of the invention is not limited to the determination of transmission type spectra. Liquids and pastes can also be examined utilizing the screen cell by specular and diffuse reflectance where the spectrometer is equipped with the accessory necessary for these determinations. Such accessories are commonly available for UV, VIS, NIR and FTIR spectrometers.

What is claimed is:

1. A method of analyzing a specimen comprising the steps of forming a specimen support of a rigid material that is non-reactive to water, acidic substances and solvents having a pair of opposed surfaces and having a plurality of unobstructed holes in a rigid surface disposed between said pair of opposed surfaces, the axes of said holes being substantially perpendicular to said opposed surfaces; enclosing each hole with an unsupported layer of a specimen to be analyzed, said specimen being selected from the group consisting of liquid, solid, paste or powder, said holes sized to retain a specimen to be analyzed enclosing said hole when said specimen support is positioned so that said opposed surfaces are vertical; positioning said support so that the axes of said holes are horizontal; directing a beam of infrared light through the holes and through the layer of said specimen enclosing each hole; and generating a wavelength spectrum of said beam passing through said layer.

2. The method of claim 1 wherein said specimen is a liquid specimen.

3. The method of claim 1 wherein said specimen support comprises a pair of opposed surfaces having a plurality of unobstructed holes in a screen disposed between said pair of opposed surfaces.

4. The method of claim 2 wherein the largest dimension of each of said holes is in the range of 0.1 to about 2 mm.

5. The method of claim 1 wherein the largest dimension of each of said holes is in the range of 0.5 to about 1 mm.

6. The method of claim 1 wherein the cross-sectional area of each of said holes is in the range of 0.9 to 1.1 square millimeters.

7. An analytic specimen support for insertion in a spectrometer comprising a pair of opposed generally flat surfaces composed of rigid material that is non-reactive to water, acidic substances and solvents and having a plurality of unobstructed holes in a screen disposed between said pair of opposed, generally flat surfaces, the outer edges of said support being adapted to be placed vertically in said spectrometer; the screen being positioned with respect to said surfaces such that when the support is placed vertically in a spectrometer the unobstructed holes are positioned in the path of the spectrometer beam; the cross-sectional area of each hole is in the range of 0.01 to 4 $mm^2$ sufficient to retain about 0.1 microliter of liquid spanning said hole for at least 4 seconds when said screen is in a vertical position, the liquid being held in said hole by the surface tension of the liquid.

8. The support of claim 7 wherein the cross-sectional area of each of said holes is in the range of 0.25 to 1.1 $mm^2$.

* * * * *